United States Patent
Rainone et al.

(10) Patent No.: US 8,280,471 B2
(45) Date of Patent: Oct. 2, 2012

(54) FIBER OPTIC BASED DETECTION OF AUTOFLUORESCENT BACTERIAL PATHOGENS

(75) Inventors: Mike Rainone, Palestine, TX (US);
Erica M. Phillips, Woodstock, GA (US);
Richard Hantke, Chicago, IL (US);
Shawn R. Feaster, Duluth, GA (US);
Daniel Baird, Woodstock, GA (US);
Thomas Edward Plowman, Cary, NC (US); Talbot Presley, Palestine, TX (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1225 days.

(21) Appl. No.: 11/954,867

(22) Filed: Dec. 12, 2007

(65) Prior Publication Data

US 2009/0156943 A1  Jun. 18, 2009

(51) Int. Cl.
*A61B 5/1455* (2006.01)
(52) U.S. Cl. .................... 600/310; 600/314; 600/342
(58) Field of Classification Search ............ 600/310, 600/314, 316–317, 322, 326, 341–342, 344, 600/476–478; 436/63–64
See application file for complete search history.

(56) References Cited

U.S. PATENT DOCUMENTS

| | | | |
|---|---|---|---|
| 4,200,110 A | 4/1980 | Peterson et al. | |
| 4,548,505 A | 10/1985 | Ono | |
| 4,803,992 A * | 2/1989 | Lemelson | 600/342 |
| 4,846,548 A | 7/1989 | Klainer | |
| 4,847,198 A | 7/1989 | Nelson et al. | |
| 5,000,901 A | 3/1991 | Iyer et al. | |
| 5,082,630 A | 1/1992 | Partin et al. | |
| 5,108,899 A | 4/1992 | Allen | |
| 5,239,998 A | 8/1993 | Krauthamer | |
| 5,408,999 A | 4/1995 | Singh et al. | |
| 5,452,723 A * | 9/1995 | Wu et al. | 600/317 |
| 5,701,902 A | 12/1997 | Vari et al. | |

(Continued)

FOREIGN PATENT DOCUMENTS

EP    0482960 A1    4/1992

(Continued)

OTHER PUBLICATIONS

Cervantes-Martinez et al., *Detection of Bacterial Infection of Agave Plants by Laser-Induced Fluorescence*, Applied Optics. vol. 41, No. 13, May 1, 2002, pp. 2541-2545.

(Continued)

*Primary Examiner* — Eric Winakur
*Assistant Examiner* — Chu Chuan (JJ) Liu
(74) *Attorney, Agent, or Firm* — Dority & Manning, P.A.

(57) ABSTRACT

Disclosed are methods and devices for continuous in vivo monitoring of a potential bacterial infection site. Disclosed devices may be utilized to alert patients and/or health care providers to the presence of pathogenic bacteria at an early stage of a hospital acquired infection, thereby providing for earlier intervention. Disclosed methods utilize optical fibers to deliver an excitation signal to an area in which pathogenic bacteria may exist. In the presence of the excitation signal, bacterial pathogens may autofluoresce with a unique spectral signature. Upon generation of a fluorescent emission, an optically detectable emission signal may be transmitted to a detection/analysis device. Analysis of the characteristics of the emission signal produced in response to the excitation signal may be used to determine the presence or concentration of pathogens at the site of inquiry, following which real time information may be transmitted to medical personnel via a wireless transmission system.

22 Claims, 13 Drawing Sheets

U.S. PATENT DOCUMENTS

| | | | |
|---|---|---|---|
| 5,722,397 A * | 3/1998 | Eppstein | 600/310 |
| 5,773,835 A | 6/1998 | Sinofsky | |
| 5,809,185 A | 9/1998 | Mitchell | |
| 5,862,803 A | 1/1999 | Besson et al. | |
| 5,938,617 A * | 8/1999 | Vo-Dinh | 600/476 |
| 5,968,766 A | 10/1999 | Powers | |
| 5,976,885 A | 11/1999 | Cohenford et al. | |
| 6,008,889 A | 12/1999 | Zeng et al. | |
| 6,026,323 A | 2/2000 | Skladnev et al. | |
| 6,031,232 A | 2/2000 | Cohenford et al. | |
| 6,040,194 A | 3/2000 | Chick et al. | |
| 6,058,352 A | 5/2000 | Lu et al. | |
| 6,069,689 A | 5/2000 | Zeng et al. | |
| 6,289,238 B1 | 9/2001 | Besson et al. | |
| 6,377,842 B1 | 4/2002 | Pogue et al. | |
| 6,411,907 B1 | 6/2002 | Lu et al. | |
| 6,441,747 B1 | 8/2002 | Khair et al. | |
| 6,485,962 B1 | 11/2002 | Tabacco et al. | |
| 6,571,118 B1 | 5/2003 | Utzinger et al. | |
| 6,659,947 B1 | 12/2003 | Carter et al. | |
| 6,671,540 B1 | 12/2003 | Hochman | |
| 6,738,651 B1 | 5/2004 | Jackson | |
| 6,749,574 B2 | 6/2004 | O'Keefe | |
| 6,802,811 B1 | 10/2004 | Slepian | |
| 6,961,599 B2 | 11/2005 | Lambert et al. | |
| 7,096,053 B2 | 8/2006 | Loeb et al. | |
| 7,110,886 B2 | 9/2006 | Ito et al. | |
| 7,190,457 B2 | 3/2007 | Tabacco et al. | |
| 7,252,659 B2 | 8/2007 | Shehada et al. | |
| 7,292,323 B2 | 11/2007 | Artsyukhovich et al. | |
| 7,294,105 B1 | 11/2007 | Islam | |
| 2003/0139667 A1 | 7/2003 | Hewko et al. | |
| 2003/0208113 A1* | 11/2003 | Mault et al. | 600/316 |
| 2004/0063216 A1 | 4/2004 | Lubocki | |
| 2004/0078219 A1 | 4/2004 | Kaylor et al. | |
| 2004/0204651 A1* | 10/2004 | Freeman et al. | 600/478 |
| 2005/0101841 A9 | 5/2005 | Kaylor et al. | |
| 2005/0234526 A1 | 10/2005 | Gilhuly et al. | |
| 2005/0272027 A1 | 12/2005 | Cheng et al. | |
| 2006/0159589 A1 | 7/2006 | Saxena | |
| 2006/0177891 A1 | 8/2006 | Kishen et al. | |
| 2006/0253005 A1 | 11/2006 | Drinan et al. | |

FOREIGN PATENT DOCUMENTS

| | | |
|---|---|---|
| EP | 1138343 A1 | 10/2001 |
| EP | 1820517 A2 | 8/2007 |
| WO | WO 9957529 A1 | 11/1999 |
| WO | WO 0169199 A2 | 9/2001 |
| WO | WO 0185637 A2 | 11/2001 |
| WO | WO 03083454 | 10/2003 |
| WO | WO 03083454 A1 | 10/2003 |
| WO | WO 2005045393 A2 | 5/2005 |
| WO | WO 2006009910 A2 | 1/2006 |
| WO | WO 2006076810 A1 | 7/2006 |
| WO | WO 2006086578 A1 | 8/2006 |

OTHER PUBLICATIONS

John et al., *Determination of bacterial activity by use of an evanescent-wave fiber-optic sensor*, Applied Optics, vol. 41, No. 34, Dec. 1, 2002, pp. 7334-7338.

Search Report and Written Opinion for PCT/IB2008/053654 dated Jun. 12, 2009, 15 pages.

Related U.S. Patent Applications.

Bhatta et al., "Rapid Identification of Microorganisms by Intrinsic Fluorescence," Imaging Manipulation, and Analysis of Biomolecules and Cells: Fundamentals and Applications III, Proc. of SPIE vol. 5699, pp. 9-18 (2005).

Bronk et al., "Variability of Steady-State Bacterial Fluorescence with Respect to Growth Conditions," Applied Spectroscopy, vol. 47, No. 4, pp. 436-449 (1993).

Brookner et al., "Effects of biographical variables on cervical fluorescence emission spectra," Journal of Biomedical Optics, vol. 8, No. 3, pp. 479-483 (Jul. 2003).

Cahn et al., "Multivariate Calibration of Infrared Spectra for Quantitative Analysis Using Designed Experiments," Applied Spectroscopy, vol. 42, No. 5, pp. 865-872, (1988).

Giana, et al., Rapid Identification of Bacterial Species by Fluorescence Spectroscopy and Classification Through Principal Components Analysis, Journal of Fluorescence, vol. 13, No. 6, pp. 489-493 (Nov. 2003).

Kania et al., "Semiconductor Based UV Light Source for Autofluorescence Imaging," Photonics Applications in Astronomy, Communications, Industry, and High-Energy Physics Experiments IV, Proc. of SPIE vol. 6159, pp. 61593K-1-61593K-4, 2006.

Li et al., "Autofluorescence spectroscopic characteristics of nasopharyngeal carcinoma and normal tissue," Fourth International Conference on Photonics and Imaging in Biology and Medicine, Proc. of SPIE, vol. 6047, pp. 60472X-1-60472X-6, 2006.

Lu et al., "Shaping Biodegradable Polymers as Nanostructures: Fabrication and Applications", Drug Discovery Today, Technologies, vol. 2, No. 1, pp. 97-102 (2005).

Na et al., "Autofluorescence spectrum of skin: component bands and body site variations," Skin Research and Technology, vol. 6, pp. 112-117, 2000.

Padilla-Ybarra, J, et al. "UV Induced Autofluorescence Spectroscopy in Barrett's Esophagus", SPIE, vol. 3197, pp. 54-59, 1997.

Plowman et al., "Femtomolar sensitivity using a channel-etched thin film waveguide fluoroimmunosensor," Biosensors & Bioelectronics, vol. 11, No. 1/2, pp. 149-160 (1996).

Plowman et al., "Multiple-Analyte Fluoroimmunoassay Using an Integrated Optical Waveguide Sensor (Abstract)," Anal. Chem. vol. 71, No. 19, pp. 4344-4352 (1999).

Plowman, "Silicon oxynitride integrated optical waveguide fluoroimmunosensor: multiple analyte sensing," Doctoral Dissertation, Duke University, 1999.

Plowman et al., "Surface sensitivity of SiON integrated optical waveguides (IOWs) examined by IOW-attenuated total reflection spectrometry and IOW-Raman spectroscopy," Thin Solid Films, vol. 243, pp. 610-615 (1994).

Plowman et al., "Waveguide Multi-Channel Immunoassay using Photo-Deprotection Immobilization," SPIE vol. 3603, pp. 163-169 (Jan. 1999).

Qu et al, "Fluorescence spectral imaging for characterization of tissue based on multivariate statistical analysis," J. Opt. Soc. Am. A, vol. 19, No. 9, pp. 1823-1831 (Sep. 2002).

Saxena et al., "Autofluorescence-Based Bacterial Detection Using an Optical Fiber," Optical Diagnostics of Living Cells V, Proc. of SPIE vol. 4622, pp. 106-111 (2002).

Sunde, "Fluorescence in situ hybridization (FISH) for Direct Visualization of Bacteria in Periapical Lesions of Asymptomatic Root-Filled Teeth", Microbiology, vol. 149, pp. 1095-1102 (2003).

Thoumas et al., "Imaging Characteristics of Alkaline-Encrusted Cystitis and Pyelitis," AJR, vol. 178, pp. 389-392 (Feb. 2002).

Utzinger et al., "Fiber optic probes for biomedical optical spectroscopy," Journal of Biomedical Optics, vol. 8, No. 1, pp. 121-147 (Jan. 2003).

Utzinger et al., "Fibre Optic Probes in Optical Spectroscopy, Clinical Applications," Encyclopedia of Spectroscopy and Spectrometry, Academic Press, pp. 512-528 (1999).

Lakowicz, et al., "Emerging Biomedical and Advanced Applications of Time-Resolved Fluorescence Spectroscopy" *Journal of Fluorescence*, vol. 4, No. 1, 1994.

* cited by examiner

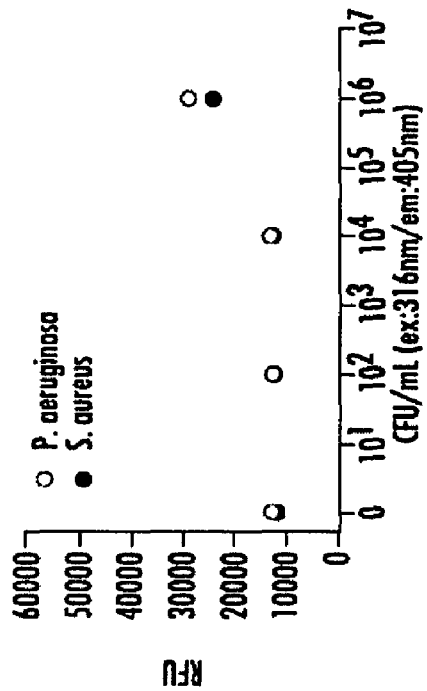
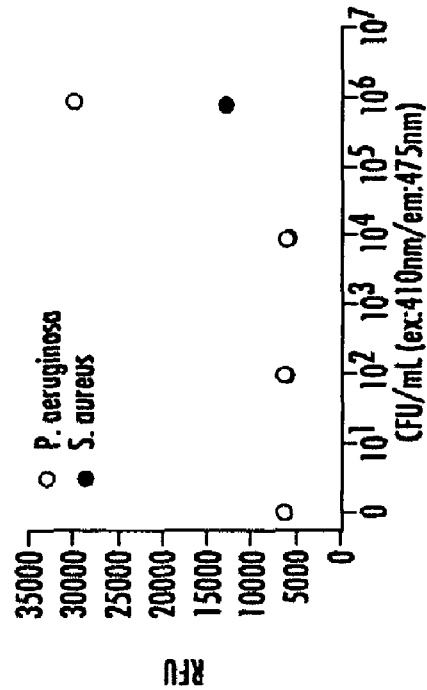
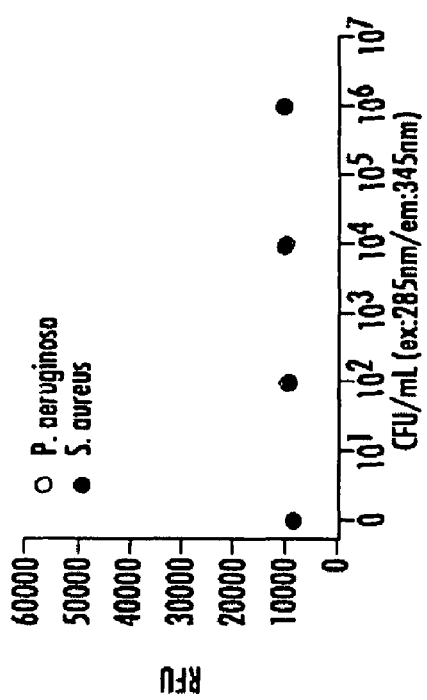
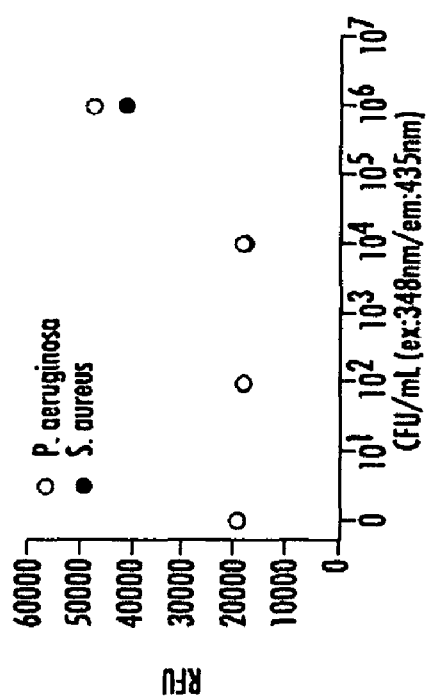

FIBER OPTIC BASED DETECTION OF AUTOFLUORESCENT BACTERIAL PATHOGENS

BACKGROUND

Nosocomial or hospital acquired infections (HAI) have been estimated by the World Health Organization (WHO) to kill between 1.5 and 3 million people every year worldwide. Though commonly referred to as hospital acquired infections, nosocomial infections result from treatment in any healthcare service unit, and are generally defined as infections that are secondary to the patient's original condition. In the United States, HAIs are estimated to occur in 5 percent of all acute care hospitalizations, resulting in more than $4.5 billion in excess health care costs. According to a survey of U.S. hospitals by the Centers for Disease Control and Prevention (CDC), HAIs accounted for about 1.7 million infections and about 99,000 associated deaths in 2002. The CDC reported that "[t]he number of HAIs exceeded the number of cases of any currently notifiable disease, and deaths associated with HAIs in hospitals exceeded the number attributable to several of the top ten leading causes of death in U.S. vital statistics" (Centers for Disease Control and Prevention, "Estimates of Healthcare Associated Diseases," May 30, 2007).

HAIs, including surgical site infections (SSIs), catheter related blood stream infections (CRBSIs), urinary tract infections (UTIs), ventilator associated pneumonia (VAP), and others, may be caused by bacteria, viruses, fungi, or parasites. Surgical site infections acquired in a hospital setting are commonly caused by bacterial organisms, such as *Escherichia coli, Staphylococcus aureus,* and *Pseudomonas aeruginosa*. According to the CDC's Guideline for Prevention of Surgical Site Infections (1999), these species are ranked among the top five pathogens isolated from surgical site infections between 1986 and 1996. A ranking of the percentage distributions of infections that may be directly attributable to individual pathogen species may vary slightly between SSI, CRBSI, UTI, and VAP, but it is generally understood that less than about a dozen species are responsible for the vast majority of cases (see, e.g., National Nosocomial Infections Surveillance (NNIS) Report, Data Summary from October 1986-April 1996, May, 1996).

Ongoing efforts are being made to prevent HAI through, for instance, improved hand washing and gloving materials and techniques, but such efforts have met with limited success. In an effort to better understand and curb HAIs, government regulations have increased pressure on hospitals and care-givers to monitor and report these types of infections. However, these measures are further complicated due to the prevalence of outpatient services, a result of which being that many HAIs do not become evident until after the patient has returned home. As such, infection may proceed undiagnosed for some time, complicating treatment and recovery.

A need currently exists for improved methods for diagnosing HAI. Moreover, methods that could monitor a patient, for instance a patient's surgical site, in an outpatient setting, would be of great benefit.

SUMMARY

In accordance with one embodiment, disclosed is a method for detecting the presence or amount of a pathogenic bacterium that is a source of a hospital acquired infection. For example, a method may include transmitting an excitation signal through a fiber optic cable to an in vivo environment. At the site, the excitation signal may contact a bacterial pathogen, upon which the bacterial pathogen may autofluoresce in response to the excitation signal. The autofluorescent signal of the bacterium may be transmitted to a portable detector, at which the presence or amount of the pathogen may be determined.

According to another embodiment, a portable device for detecting the presence or amount of a pathogenic bacterium that is a source of a hospital acquired infection is disclosed. A device may include, for instance, a portable enclosure containing a power source, an excitation energy source, an optical detector, a signal processor, and a signaling device for emitting a signal upon detection of the pathogenic bacterium in an environment. The device may also include a connecting device, for instance for attaching the enclosure to the clothing or body of a wearer. In addition, the device may include the fiber optic cable that may be in optical communication with the excitation source and may extend from the enclosure, so as to be inserted into the environment of interest.

Other features and aspects of the present disclosure are discussed in greater detail below.

BRIEF DESCRIPTION OF THE DRAWINGS

A full and enabling disclosure of the subject matter, including the best mode thereof, directed to one of ordinary skill in the art, is set forth more particularly in the remainder of the specification, which makes reference to the appended figures in which:

FIG. 14 summarizes the fluorescence intensity as a function of bacterial concentration at selected excitation wavelengths for *S. aureus* and *P. aeruginosa* including 285 nm excitation (FIG. 14A), 316 nm excitation (FIG. 14B), 348 nm excitation (FIG. 14C) and 410 nm excitation (FIG. 14D).

Figure 1:
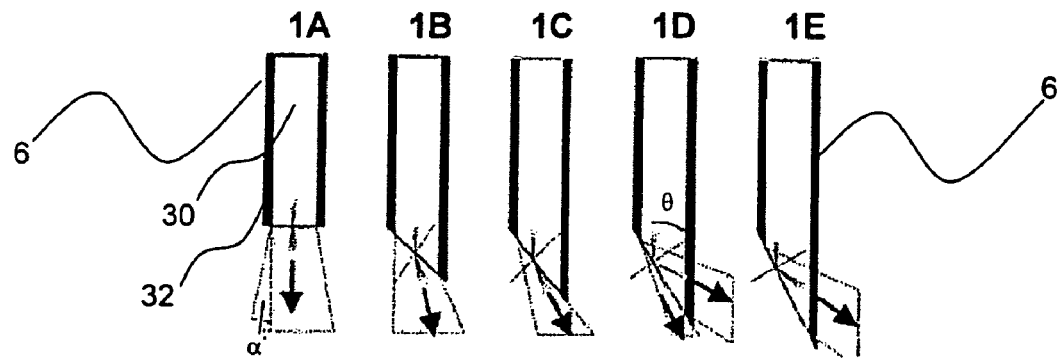
FIGS. 1A-1E are illustrative examples of optical fiber designs that are encompassed in the present disclosure.

Repeat use of reference characters in the present specification and drawings is intended to represent same or analogous features or elements.

DETAILED DESCRIPTION OF REPRESENTATIVE EMBODIMENTS

Reference now will be made in detail to various embodiments of the disclosed subject matter, one or more examples of which are set forth below. Each example is provided by way of explanation, not limitation. In fact, it will be apparent to those skilled in the art that various modifications and variations may be made in the present disclosure without departing from the scope or spirit of the subject matter. For instance, features illustrated or described as part of one embodiment, may be used on another embodiment to yield a still further embodiment. Thus, it is intended that the present disclosure covers such modifications and variations as come within the scope of the appended claims and their equivalents.

The present disclosure is generally directed to methods for detection of bacterial HAI. In one particular embodiment, disclosed methods may be utilized for continuous in vivo monitoring of a potential bacterial infection site and may be utilized to alert patients and/or health care providers to the presence of pathogenic bacteria at an early stage of infection, thereby providing for earlier intervention and improved recovery rates from bacterial infection.

In general, any autofluorescent bacterial source of HAI may be detected according to disclosed methods. For instance, while *Escherichia coli, Staphylococcus aureus,* and *Pseudomonas aeruginosa* may be of particular interest in certain embodiments, disclosed methods are not limited to these bacteria. Other common bacterial sources of HAI that may be detected according to disclosed methods include, without limitation, coagulase-negative *staphylococci, Enterococcus* spp., *Enterobacter* spp., *Klebsiella pneumoniae, Proteus mirabilis, Streptococcus* spp., and so forth.

Presently disclosed methods utilize optical fibers to deliver an excitation signal to an area in which pathogenic bacteria may exist. In the presence of the excitation signal, bacterial pathogens may autofluoresce with a unique spectral signature. Upon generation of a fluorescent emission, an optically detectable emission signal may be transmitted to a detection/ analysis device via the same optical fiber(s) as are utilized to deliver the excitation signal or different optical fibers. Analysis of the characteristics of the emission signal produced in response to the excitation signal may be used to determine the presence or concentration of pathogens at the site of inquiry and provide a route for early detection of a nosocomial infection. For instance, in one particular embodiment, information regarding the presence or concentration of a bacterial pathogen at the site of inquiry may be transmitted to appropriate medical personnel via a wireless transmission regime.

An optical fiber may be located at a site according to any suitable method. For instance, an optical fiber may be located at an in vivo site of interest during a medical procedure. In one particular embodiment, the site of interest may be a surgical site and an optical fiber may be located within all or a portion of the surgical site prior to close of the surgery. In another embodiment, an optical fiber may be located within a wound site, for instance during cleaning, dressing changing, and so forth, at the wound site.

Beneficially, optical fibers may be formed of biocompatible materials that may remain at a site of interest for a relatively long period of time, for instance to monitor a site for infection throughout the healing process and until high potential for bacterial infection has past. In addition, at the time of removal, optical fibers may be easily removed from a site without the necessity of causing excessive tissue damage at the site, due to the small cross-section of the fibers.

FIG. 1 schematically illustrates several embodiments of optical fibers 6 as may be utilized according to certain disclosed detection methods. An optical fiber may include a core 30, through which light may travel, and an external cladding layer 32. The difference in the index of refraction between the core material and the clad material defines the critical angle θ at which total internal reflection takes place at the core/clad interface. Thus, light that impinges upon the interface at an angle greater than the critical angle is completely reflected, allowing the light to propagate down the fiber.

Optical fibers for use as disclosed herein may generally include multi-mode fibers having a core diameter greater than about 10 micrometers (μm). The preferred core diameter in any particular embodiment may depend upon the characteristics of excitation signal and/or emission signal that are expected to travel through the fiber, among other system parameters. For instance, in those embodiments in which a laser is the excitation source, a core diameter may be between about 50 μm and about 100 μm, or about 80 μm in one embodiment. In other embodiments, for instance in those embodiments in which an excitation light source produces less coherent radiation, such as a multi-wavelength light emitting diode (LED), for example, it may be preferable to utilize an optical fiber having a larger core diameter, for instance between about 90 μm and about 400 μm.

The core/clad boundary of a fiber may be abrupt, as in a step-index fiber, or may be gradual, as in a graded-index fiber. A graded-index fiber may be preferred in some embodiments, as graded index fibers may reduce dispersion of multiple modes traveling through the fiber. This is not a requirement however, and step-index fibers may alternatively be utilized, particularly in those embodiments in which an optical fiber is of a length such that dispersion will not be of great concern.

An optical fiber may be formed of sterilizable, biocompatible materials that may be safely placed and held at a potential infection site, and in one particular embodiment, at a surgical site. For example, an optical fiber formed of any suitable type of glass may be used, including, without limitation, silica glass, fluorozirconate glass, fluoroaluminate glass, any chalcogenide glass, or so forth may form the core and/or the clad.

Polymer optical fibers (POF) are also encompassed by the present disclosure. For instance, an optical fiber formed of suitable acrylate core/clad combinations, e.g., polymethyl methacrylates, may be utilized. It may be preferred in some embodiments to utilize a multi-core POF so as to lower losses common to POF due to bending of the fiber. For instance, this may be preferred in those embodiments in which an optical fiber may be located at an in vivo site of inquiry in a non-linear conformation.

The end of a fiber may be shaped as desired. For instance, and as illustrated in FIGS. 1A-1E, polishing or otherwise forming a specific angle at the end face of a fiber may maintain the acceptance angle α and collection efficiency of the fiber, while rotating the field of view of the fiber, as depicted by the arrows on FIGS. 1A-1E. Depending upon the angle at the fiber end, light may enter the fiber from angles up to about 90° of the fiber axis (e.g., as shown at FIG. 1E) (see, e.g., Utzinger, et al., Journal of Biomedical Optics, 8(1):121-147, 2003).

An optical fiber may be formed so as to detect an emission signal at locations along the length of the fiber, in addition to at the terminal end of the fiber. For instance, at locations along the length of the fiber the clad may be etched, generally with a predetermined angle, such that excitation light may exit the fiber and/or detectable signals emitted from a bacterial pathogen may enter the optical fiber at these locations. For example, the clad of a fiber may be bent or otherwise notched at a predetermined angle to form a 'window' in the fiber. Thus, a single optical fiber may detect signals from transformed bacterial over a larger area.

A fiber optic sensor for use as described herein may include a fiber optic cable comprised of a single optical fiber or a plurality of individual fibers, depending upon the specific design of the sensor. For instance, a plurality of optical fibers may be joined to form a single fiber cable of a size to be located at an in vivo site of interest (e.g., less than about 1.5 mm in cross-sectional diameter). Moreover, certain optical fibers of a fiber optic cable may be utilized to deliver an excitation signal to an area, while other optical fibers may be utilized to carry emission signals from the area back to a photodetector, as discussed further herein.

Figure 2A:
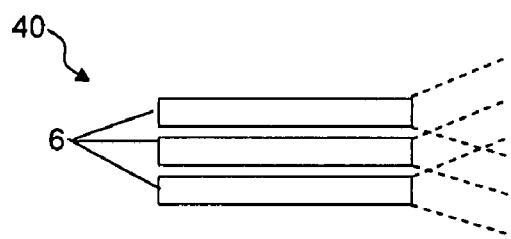
FIGS. 2A-2C are schematic representations of an optical fiber bundle as may be incorporated in a device as disclosed herein.
Figure 2B:
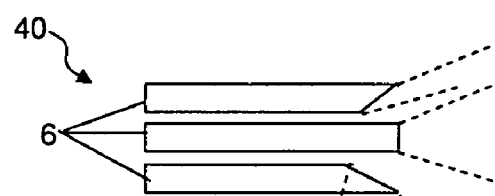
Figure 2C:
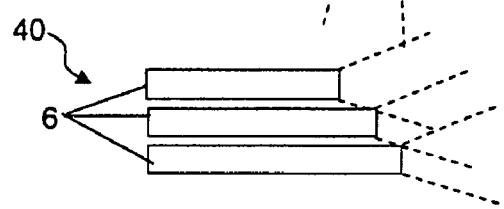

When utilizing a plurality of optical fibers in a fiber optic bundle or cable, individual fibers may be formed and arranged in relation to one another so as to provide a wider angle of detection. For instance, FIGS. 2A-2C illustrate several different embodiments of a fiber cable 40 comprising multiple optical fibers 6 in the bundle. For instance, as shown at FIG. 2A, through location of a plurality of fiber ends at a single cross-sectional area, improved light collection may be attained, as the total field area covered by the combined fibers will be larger than that for a single fiber (as indicated by the dashed lines of the figure). In the embodiment illustrated in FIG. 2B, the geometry of the end face of different fibers contained in the cable 40 may be different from one another, so as to allow light collection from a variety of different directions. In the embodiment illustrated in FIG. 2C, fiber ends are staggered over a length, so as to increase the axial length of the light delivery/collection area and increase the area of inquiry in an axial direction. Of course, combinations of such designs, as well as other fiber designs for improving the collection of a signal area, including methods as discussed above as well as methods as are generally known to those in the art, may be utilized as well.

A bundle or cable of optical fibers 40 may generally be held as a cohesive unit with any biocompatible sheath that may hold the unit together while maintaining flexibility of the fibers. For instance, a fiber optic cable may include an outer sheath of a flexible polyurethane.

Figure 3:
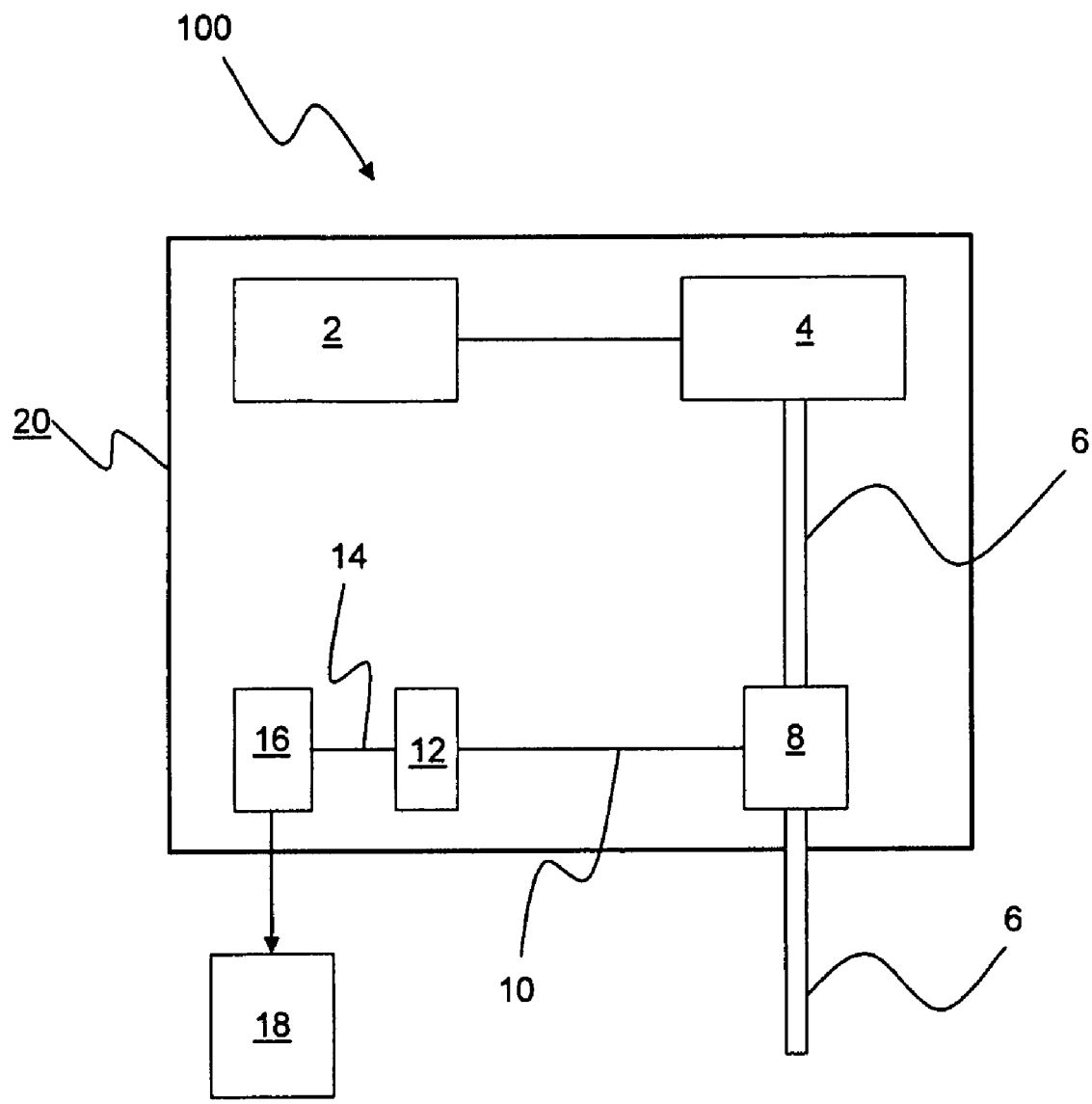
FIG. 3 schematically illustrates one embodiment of a portable device as disclosed herein.

In accordance with the present technology, one or more optical fibers may be utilized as a portion of a sensor that may be contained by use of a portable device, one embodiment of which is schematically illustrated in FIG. 3. As may be seen in FIG. 3, device 100 may include several components that may be housed within an enclosure 20.

Enclosure 20 may be, for example, a molded plastic enclosure of a size so as to be easily carried by or attached to a wearer. For instance, enclosure 20 may include clips, loops, or so forth so as to be attachable to a patient's clothing or body. In one embodiment, enclosure 20 may include an adhesive surface, and may be adhered directly to a patient's skin. In general, enclosure 20 may be relatively small, for instance less than about 10 cm by about 8 cm by about 5 cm, so as to be inconspicuously carried by a patient and so as to avoid impedance of a patient's motion. Enclosure 20 may completely enclose the components contained therein, or may partially enclose the components contained therein. For example, enclosure 20 may include an access port (not shown) that may provide access to the interior of enclosure 20. In one embodiment, an access port may be covered with a removable cover, as is known in the art.

A first component as may be held within enclosure 20 is power supply 2 that may be configured in one embodiment to supply power to an excitation source 4 as well as other of the operational components as will be later described. In an exemplary configuration, power supply 2 may correspond to a battery, however those of ordinary skill in the art will appreciate that other power supplies may be used including those that may be coupled to an external alternating current (AC) supply so that the enclosed power supply may include those components necessary to convert such external supply to a suitable source for the remaining components requiring a power source.

As previously noted, power supply 2 may be configured to supply power to excitation source 4. In the illustrated exemplary configuration, excitation source 4 may correspond to a light emitting diode (LED), however, again, such source may vary and may include, but is not limited to, laser diodes and incandescent light sources. Excitation source 4 may correspond to a white light source, a non-white multi-wavelength source, or a single wavelength source, as desired or required. In a preferred exemplary configuration, an LED may be selected due to the low power consumption of such sources. The wavelength of the excitation energy supplied by excitation source 4 may be of any suitable wavelength, from infrared (IR) to ultraviolet (UV). In general, the preferred excitation energy wavelength may depend upon any specific pathogens for which the device is designed to detect. For instance, in those embodiments in which a specific bacteria or genera is being detected, the excitation wavelength may be specific for that target. In other embodiments, however, for instance when a plurality of different pathogens are being detected, and the different pathogens respond to different excitation wavelengths, an excitation source may provide multiple wavelengths, either through combination of signals from a plurality of single wavelength sources or through a single, incoherent source, as desired.

Excitation energy source 4 is optically coupled to an optical fiber 6 as illustrated. Optical fiber 6 is configured to extend externally from enclosure 20 to the field of inquiry, e.g., within a surgical site or other wound. It should be appreciated that although optical fiber 6 is illustrated in FIG. 4 as including only a single optical fiber, such is not a specific limitation of the present disclosure as such devices may, in fact, include optical cables that include multiple fibers in alternate embodiments, and as discussed above. For instance, different optical fibers of the cable may be utilized for delivering an excitation signal and receiving an emission signal, as is known in the art. Those of ordinary skill in the art will appreciate that a single excitation energy source may be optically coupled to a plurality of optical fibers and/or fiber optic cables through utilization of suitable beam splitters, mirrors, and so forth. For instance, a first fiber optic cable may extend from an excitation source to a first detection location, and a second fiber optic cable may extend from the same or a different excitation source to a second detection location.

Moreover, as discussed previously, plural excitation energy sources may be used. In such a configuration, each excitation source may be optically coupled to one or more optical fibers such that multiple excitation wavelengths may be delivered to the field of enquiry.

Housed within enclosure 20 is an optical detector 8 coupled to optical fiber 6. Optical detector 8 may correspond to a photodiode, a photoresistor, or so forth. Optical detector 8 may include optical filters, beam splitters, and so forth that may remove background light and reduce the total input optical signal at the detector 8 to one or more diagnostically relevant emission peaks. An input signal at detector 8 may be examined and analyzed for emission peaks of interest according to any suitable method. For instance, detector 8 may comprise a plurality of notch filters, each of which may be tuned to the spectral signature of a different pathogen. In one particular embodiment, the total input optical signal to detector 8 may be deconvoluted and analyzed according to a principal components analysis (PCA) regime.

For instance, input data to detector 8 may be reduced to relevant emission peaks based on maximum variations between the input spectra. In those embodiments in which a device is designed to examine a site for a plurality of different pathogens, the total input optical signal at the detector 8 may include a plurality of diagnostically relevant emission peaks. Accordingly, detector 8 may generate an output signal representing one or more emission peaks of interest. In addition, detector 8 may provide information with regard to the strength of each signal, for instance the number of pulses of light emitted over a particular time having a particular spectral signature, and this information may be correlated to the concentration of the detected pathogen.

In one particular embodiment, the signal from detector 8 may be transmitted to signal processor 12 for further analysis according to a PCA process. A PCA regime may utilize information regarding a library of spectra derived from bacteria of a reference sample to create a reference set, wherein each of the spectra is acquired under identical conditions. Data analysis techniques that may be carried out may include spectral data compression and linear regression. Using a linear combination of factors or principal components, a reconstructed spectrum may be derived. This reconstructed spectrum may then be compared with the spectra of known specimens which serve as the basis for determination of the presence or concentration of bacteria at the site of inquiry.

U.S. Pat. No. 7,110,886 to Ito, et al., U.S. Pat. No. 6,961,599 to Lambert, et al. and U.S. Pat. No. 6,662,621 to Cohenford, et al., all of which are incorporated herein by reference thereto, describe PCA regimes as may be utilized in analysis of an emission signal. In addition, a number of computer programs are available which carry out these statistical methods, including PCR-32™ (from Bio-Rad, Cambridge, Mass., USA) and PLS-PLUS™ and DISCRIMINATE™ (from Galactic Industries, Salem, N.H., USA). Discussions of the underlying theory and calculations of suitable methods may be found in, for example, Haaland, et al., *Anal. Chem.* 60:1193-1202 (1988); Cahn, et al., *Applied Spectroscopy*, 42:865-872 (1988); and Martens, et al., Multivariate Calibration, John Wiley and Sons, New York, N.Y. (1989).

Signal processor 12 may include a microprocessor configured to evaluate the strength or other characteristics of the output signal received from detector 8 over line 10 to, e.g., detect which specific bacteria is present in the field of enquiry and to produce a detection signal that may be coupled to line 14 for passage to a signaling device 16. Accordingly, if the detection signal reaches a predetermined threshold value, corresponding to a positive determination of the target pathogen, a detectable signal may be initiated at signaling device 16. For example, a detectable signal may be initiated at a signaling device 16 upon detection of any pathogen, i.e., any detection of a targeted pathogen at all may trigger initiation of a signal at signaling device 16. Optionally, if the detection signal at signal processor 12 indicates a pathogen concentration greater than a threshold amount, which may be correlated to the strength of the input signal to signal processor 12, signaling device 16 may be triggered to initiate a signal. For instance, signaling device 16 may be preset to initiate a detectable signal when the strength of the emitted signal correlates to a bacterial concentration greater than about $10^5$ CFU/mL (colony forming units/milliliter), in one embodiment, or greater than about $10^6$ CFU/mL in another embodiment.

In an exemplary configuration, a detectable signal may initiate a visible or audible signal that may be detected by the wearer within or at the surface of the enclosure 20 by way of signaling device 16. For instance, a visible signal may optionally include utilization of a liquid crystal diode (LCD) device, or an equivalent thereof, that may provide the signal as a readable output. For example, a visual signal may be provided at a surface of the device as an instruction such as, for instance, "CALL YOUR DOCTOR", "VISIT HOSPITAL," or so forth.

In addition to or alternative to a visual and/or audible signal at the enclosure 20 itself, signaling device 16 may include a transmitter portion that, upon initiation of the detectable signal, may transmit an electromagnetic signal to receiver 18. Receiver 18 may be remote from the signaling device 16. For instance, receiver 18 may be on the wearer's body at a distance from the signaling device 16, at a location apart from the wearer's body that may be conveniently chosen by the wearer, e.g., within the wearer's home, office, or so forth, or may be at a monitoring facility, for instance at a medical facility, such that appropriate medical personal may be quickly informed of the change in status of the patient's site of inquiry. In alternative embodiments, the detectable signal may be transmitted to multiple receivers, so as to inform both the wearer and others (e.g., medical personnel) of the change in status of a site. Transmission of a signal to a remote site may be carried out with a radio frequency transmission scheme or with any other wireless-type transmission scheme, as is generally known in the art. For instance, a wireless telephone or internet communications scheme could be utilized to transmit a signal to a remote location according to known methods.

Wireless transmission systems as may be utilized in conjunction with disclosed devices and methods may include, for example, components and systems as disclosed in U.S. Pat. No. 6,289,238 to Besson, et al., U.S. Pat. No. 6,441,747 to Khair, et al., U.S. Pat. No. 6,802,811 to Slepian, U.S. Pat. No. 6,659,947 to Carter, et al., and U.S. Pat. No. 7,294,105 to Islam, all of which are incorporated in their entirety by reference.

The present disclosure may be better understood with reference to the following examples.

EXAMPLES

Methods and Materials

Spectrophotomers: Examples were performed using a Fluorolog-3 spectrofluorometer (available from HORIBA Jobin Yvon).

Bacteria: Three bacterial species were tested: *Staphylococcus aureus* (ATCC #6538), *Pseudomonas aeruginosa* (ATCC #9027), and *Escherichia coli* (ATCC #8739). These strains were tested at concentrations ranging from 107 to 102 CFU/ml, thereby bracketing the 105 CFU/ml value estimated by the CDC to represent an infection.

Buffers: Cells were suspended in normal Phosphate Buffered Saline (PBS=137 mM NaCl, 10 mM Phosphate, 2.7 mM KCl) and female human plasma, which was chosen as a simulant for human interstitial fluid. The female human plasma used had a total protein concentration of 42 mg/ml as measured by Bradford assay (Bio-Rad Laboratories). In order to simulate the lower protein concentration that could be expected to be seen in cellular interstitial fluid, protein content was reduced to about 17 mg/ml (40% original content) via centrifugation through a Microcon centrifugal 30 kDa filter (Millipore Corp).

Example 1

The emission spectra of *S. aureus* using serial dilutions of $10^3$, $10^5$, and $10^7$ CFU/mL in PBS was collected at distances ranging from 5 nm to 1000 nm. Emission and excitation slit widths were set to 5 nm. The maximum emission peaks while excited at 220 nm, 265 nm, 365 nm, or 412 nm were recorded and are tabulated below in Table 1.

TABLE 1

| Wavelength (nm) | | Relative Fluorescence Units for Bacteria in PBS | | |
|---|---|---|---|---|
| Excitation | Emission | $10^3$ (CFU/ml) | $10^5$ (CFU/ml) | $10^7$ (CFU/ml) |
| 220 | 360 | 2,300 | 2,300 | 2,420 |
| 265 | 305 | 30,900 | 18,000 | 20,300 |
|  | 365 | 111,000 | 52,200 | 55,400 |
|  | 530 | 50,700 | 64,000 | 978,000 |
|  | 585 | 16,200 | 11,000 | 9,400 |
| 365 | 412 | 39,800 | 21,700 | 10,000 |
|  | 720 | 3,760 | 6,540 | 216,000 |
| 412 | 465 | 12,000 | 6,830 | 6,500 |
| 465 | n/a | n/a | n/a | n/a |

Figure 4A:
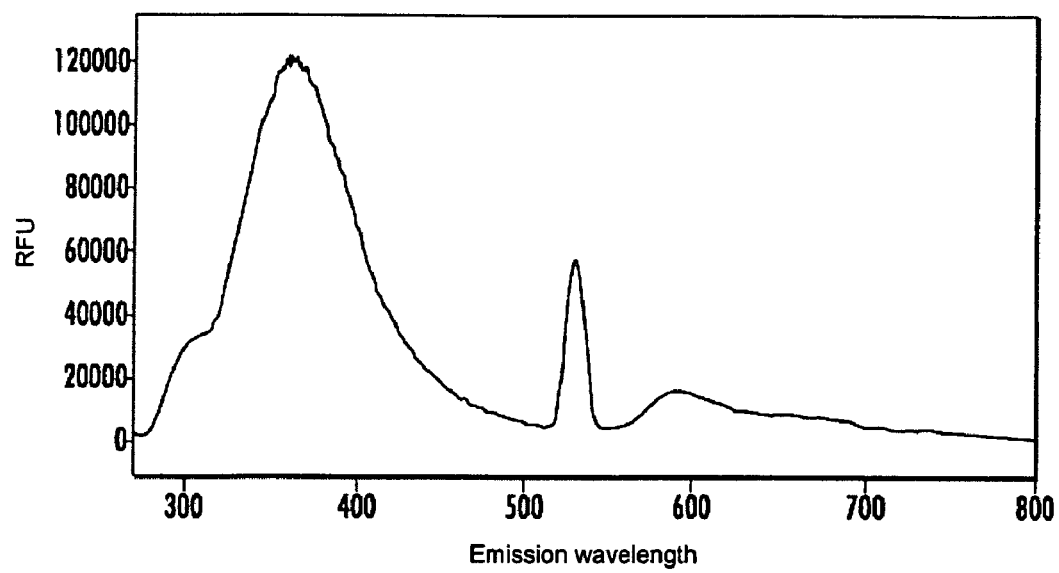
FIG. 4 graphically illustrates representative emission spectra of *S. aureus* in a phosphate buffered saline (PBS) and excited at 265 nm at a bacteria loading level of $10^4$ CFU/mL (FIG. 4A) and at $10^7$ CFU/mL (FIG. 4B)
Figure 4B:
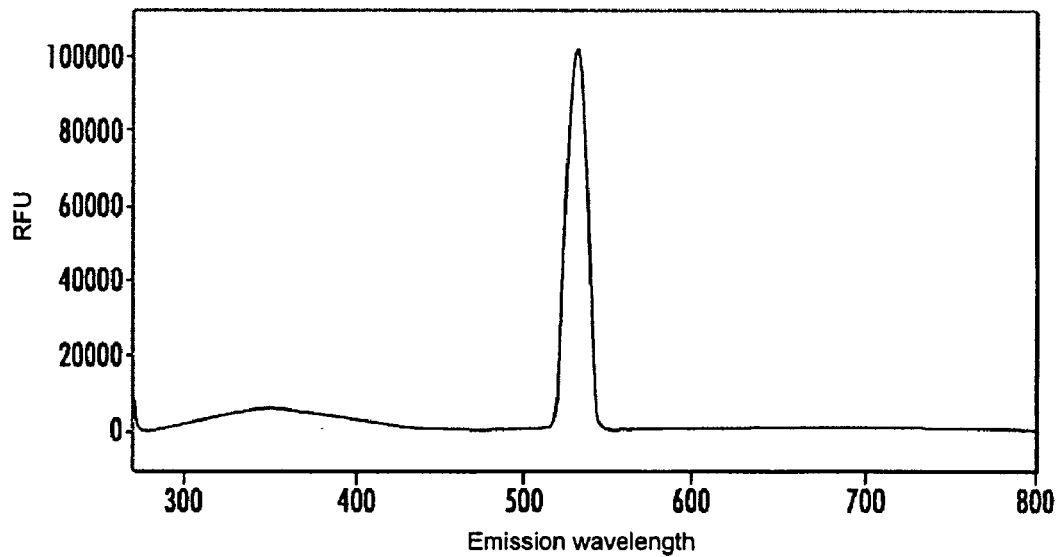

FIG. 4 illustrates the emission spectra of *S. aureus* excited at 265 nm in PBS at a concentration of $10^4$ CFU/mL (FIG. 4A) and at $10^7$ CFU/mL. As may be seen, the peak around 530 nm tends to increase in intensity relative to all others as a function of concentration. These emission profiles indicate a change in fluorescence intensity due to concentration.

Example 2

Figure 5:
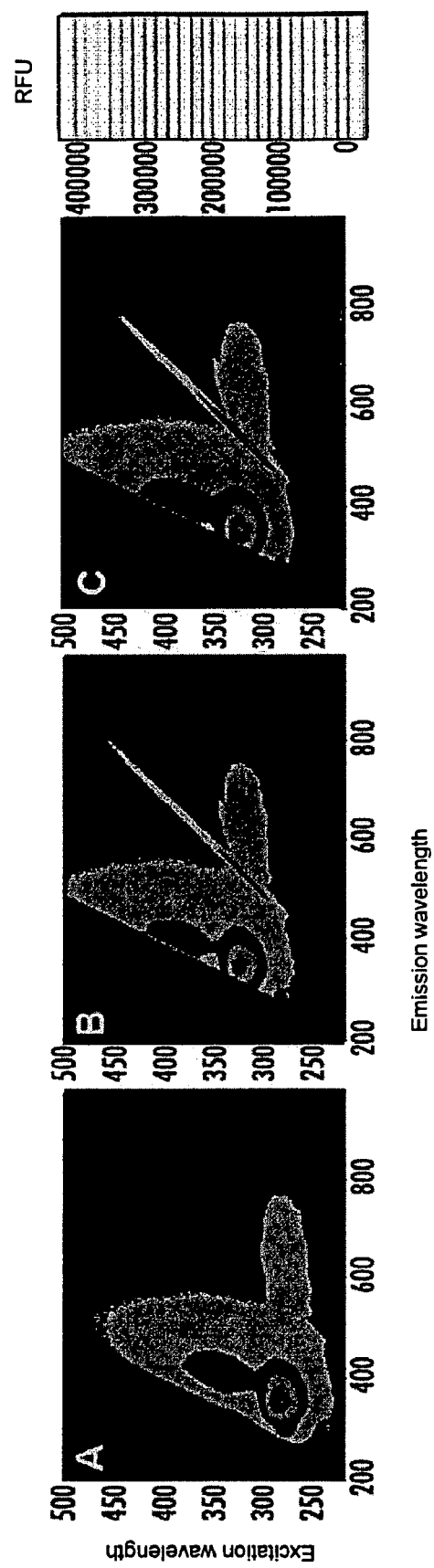
FIG. 5 illustrates contour excitation/emission fingerprint spectra at a $10^4$ CFU/mL bacterial load in PBS for *S. aureus* (FIG. 5A), *P. aeruginosa* (FIG. 5B), and *E. coli* (FIG. 5C)
Figure 6A:
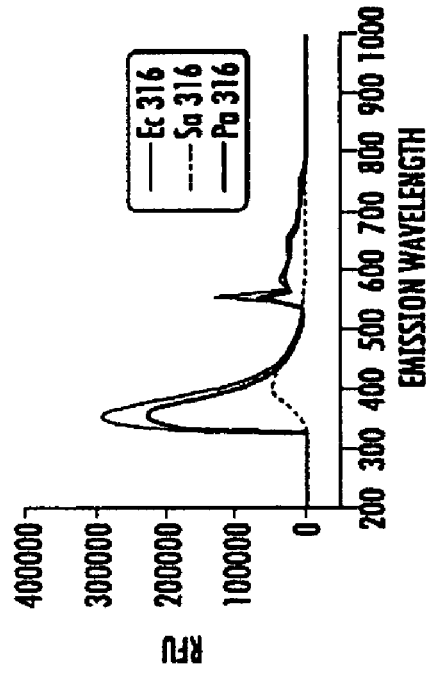
FIG. 6 graphically illustrates the emission spectra of *E. coli* (Ec), *S. aureus* (Sa), and *P. aeruginosa* (Pa) in PBS at various excitation wavelengths including 285 nm (FIG. 6A), 316 nm (FIG. 6B), 348 nm (FIG. 6C), and 410 nm (FIG. 6D)
Figure 6B:
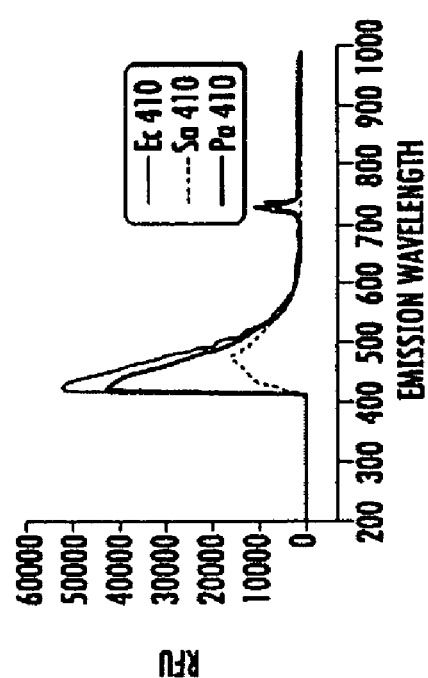
Figure 6C:
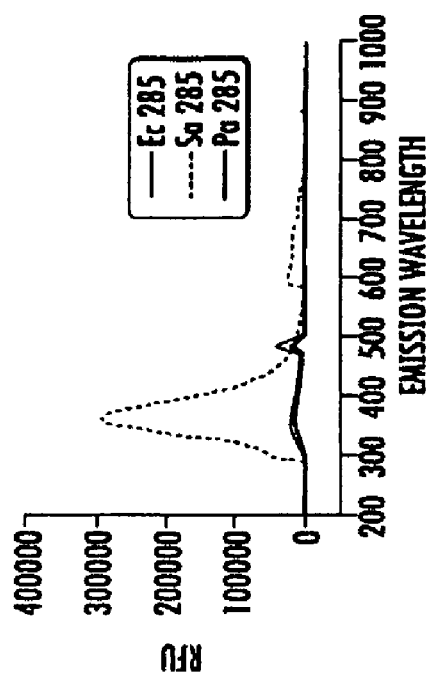
Figure 6D:
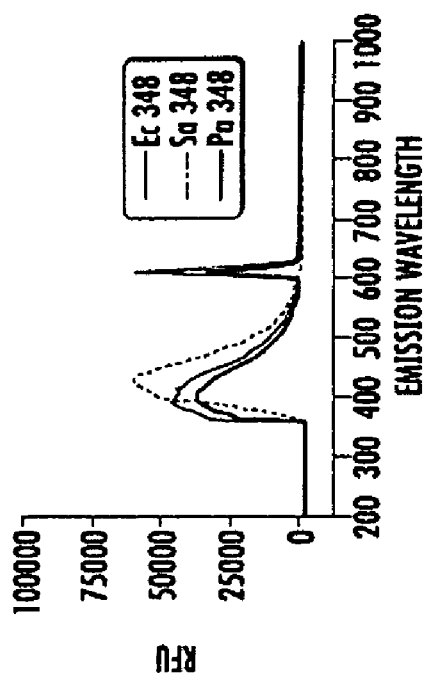

Fluorescence contour excitation/emission fingerprint spectra of *S. aureus, P. aeruginosa,* and *E. coli* at $10^4$ CFU/mL in normal PBS were collected using excitation wavelengths spanning 220 nm to 500 nm, stepping through at 2.33 nm intervals. Emissions were collected from 200 nm to 1000 nm suppressing both first order and second order scattering events. Resulting contour fingerprint spectra are shown in FIG. 5 including results for *S. aureus* in FIG. 5A, *P. aeruginosa* in FIG. 5B, and *E. coli* in FIG. 5C. FIG. 6 graphically illustrates the emission spectra of the different bacteria including *S. aureus* (Sa), *P. aeruginosa* (Pa), and *E. coli* (Ec) at a $10^4$ CFU/mL bacterial load at selected excitation wavelengths as shown, i.e., FIG. 6A, 285 nm; FIG. 6B, 316 nm, FIG. 6C, 348 nm, FIG. 6D, 410 nm. As may be seen, fluorescence uniqueness is suggested between species.

Example 3

Figure 7:
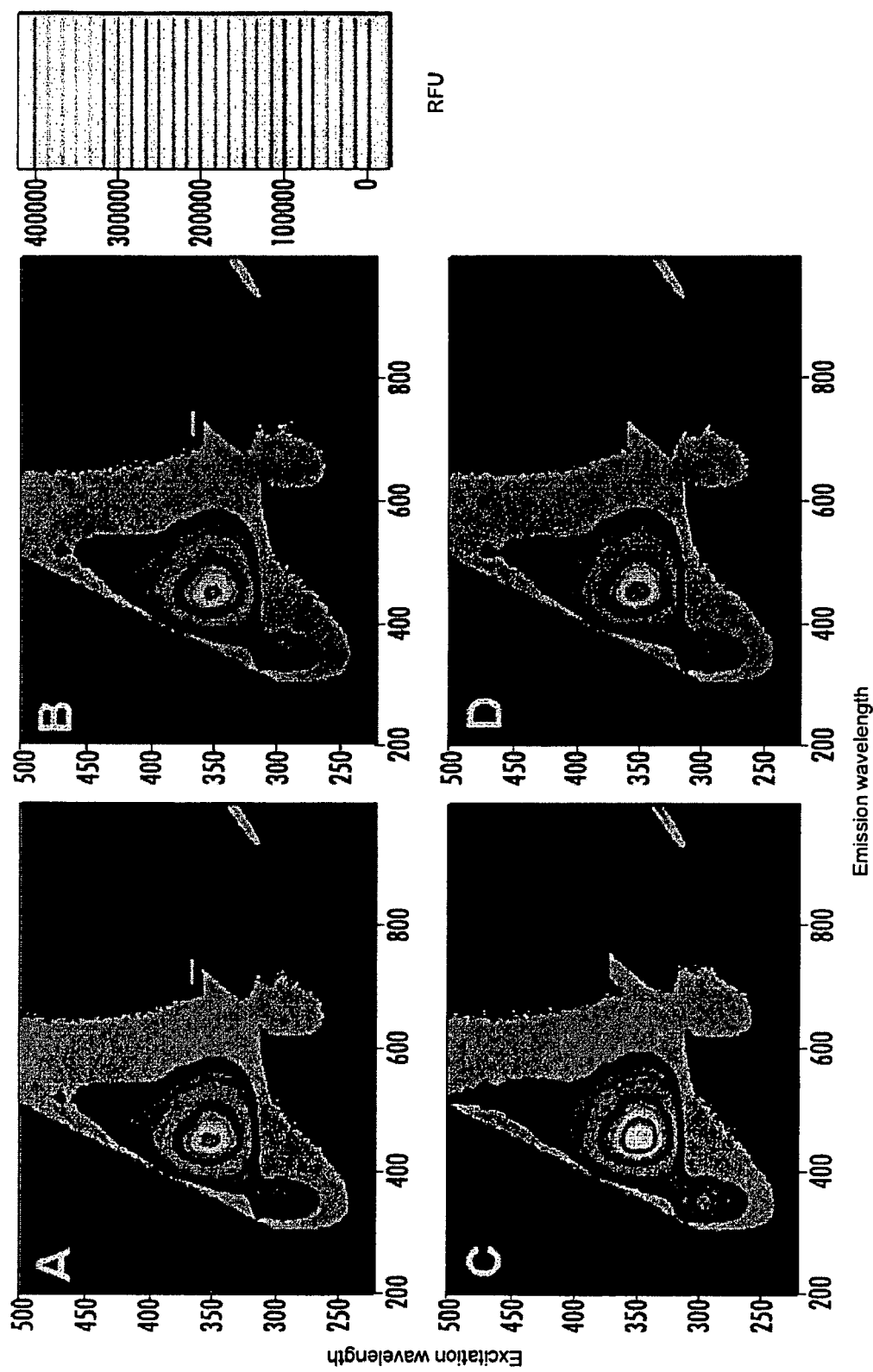
FIG. 7 illustrates contour excitation/emission fingerprint spectra at a $10^4$ CFU/mL bacterial load in female human plasma for *S. aureus* (FIG. 7A), *P. aeruginosa* (FIG. 7B), *E. coli* (FIG. 7C), and human plasma alone (FIG. 7D)

The process described above in Example 2 was repeated with *S. aureus, P. aeruginosa,* and *E. coli* at $10^4$ CFU/ml in female human plasma having a protein content of 42 mg/ml. Contour excitation/emission fingerprint spectra are shown in FIG. 7 including *S. aureus* (FIG. 7A), *P. aeruginosa* (FIG. 7B), *E. coli* (FIG. 7C) and human plasma alone (FIG. 7D). As may be seen, *E. coli* bacterial signature (FIG. 7C) is discernable even against a background composed of high protein content plasma.

Figure 8A:
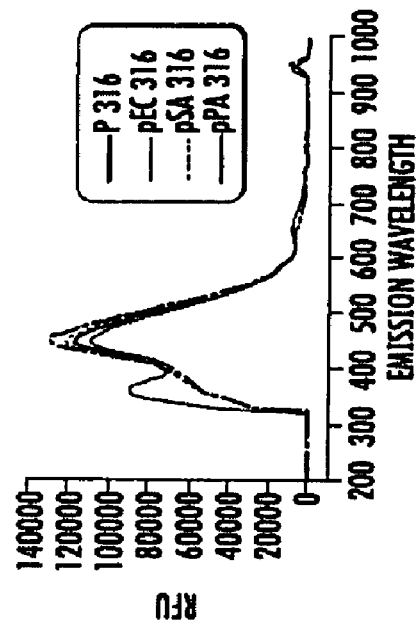
FIG. 8 graphically illustrates the emission spectra of female human plasma (P), *E. coli* (pEC), *S. aureus* (pSA), and *P. aeruginosa* (pPA) in female human plasma at various excitation wavelengths including 285 nm (FIG. 8A), 316 nm (FIG. 8B), 348 nm (FIG. 8C), and 410 nm (FIG. 8D)
Figure 8B:
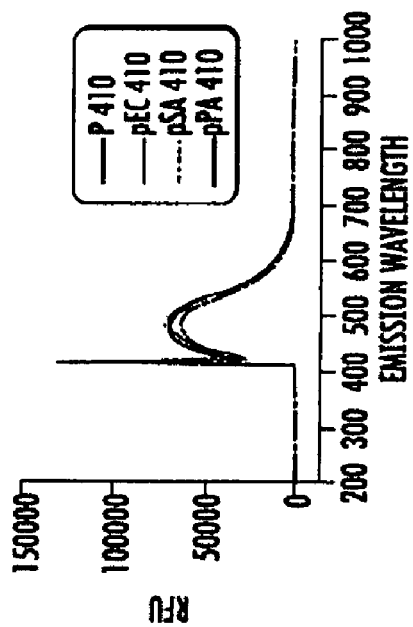
Figure 8C:
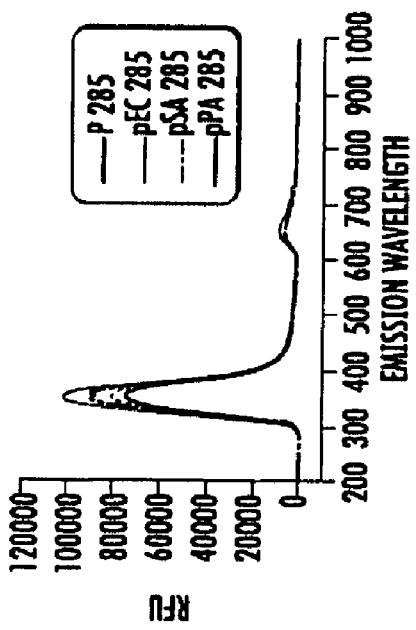
Figure 8D:
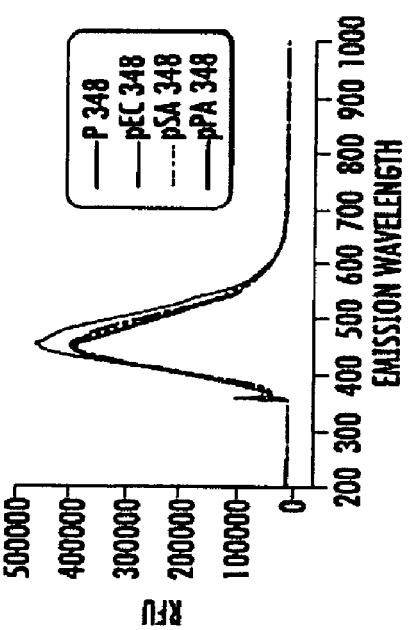

FIG. 8 graphically illustrates the emission spectra of the different bacteria in the high protein content plasma and plasma alone at selected excitation wavelengths, i.e., FIG. 8A, 285 nm; FIG. 8B, 316 nm, FIG. 8C, 348 nm, FIG. 8D, 410 nm. Materials examined included *S. aureus* (pSA), *P. aeruginosa* (pPA), *E. coli* (pEC) and human plasma alone (P). A unique excitation peak for *E. coli* is seen using an excitation wavelength of 316 nm.

Example 4

Figure 9:
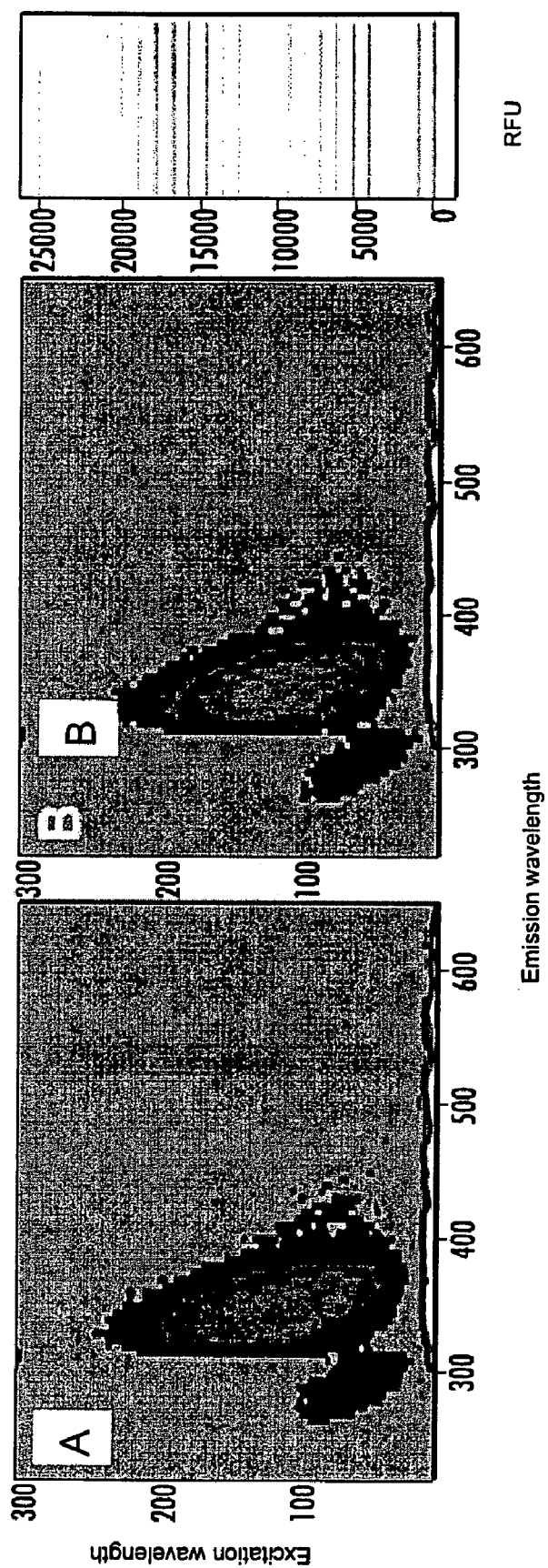
FIG. 9 illustrates synchronous fluorescence contour plots for *E. coli* at a loading level of $10^4$ CFU/mL in female human plasma (FIG. 9A) and that of female human plasma alone (FIG. 9B)

Synchronous fluorescence contour fingerprint of *E. coli* at $10^4$ CFU/ml was obtained in female human plasma (protein content of 42 mg/ml) and compared to that of the female human plasma alone. In this method, the distance between excitation and emission wavelengths was fixed in intervals of 5 nm, for window widths up to 300 nm, and scanned at wavelengths from 200 nm to 650 nm. This technique is normally used to deconvolute fluorescent signatures from complex mixtures and has been used successfully on mixtures of purified proteins. Data was collected with a Fluorolog®-3 analytical spectrofluorometer. Results are shown in FIG. 9 including FIG. 9A, which shows the results for the *E. coli* in female human plasma, and FIG. 9B, which shows the results for female human plasma alone.

Example 5

Figure 10:
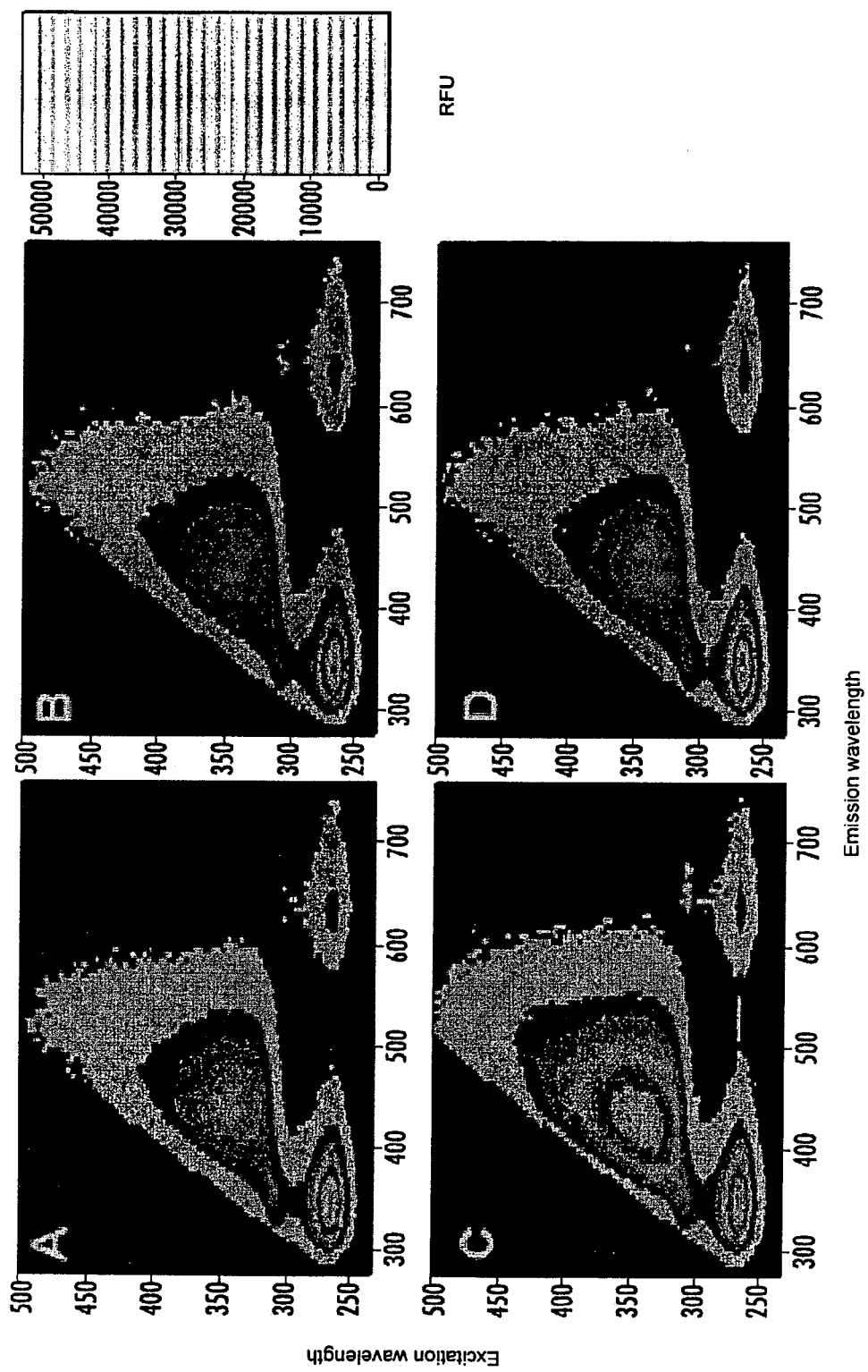
FIG. 10 illustrates contour excitation/emission fingerprint spectra for *S. aureus* in plasma having a protein content of 17 mg/mL at various loading concentrations including $10^2$ CFU/mL (FIG. 1A), $10^4$ CFU/mL (FIG. 10B), $10^6$ CFU/mL (FIG. 10C), and the plasma alone (FIG. 10D)

A fluorescence contour fingerprint of *S. aureus* at $10^6$, $10^4$, and $10^2$ CFU/ml in plasma containing a protein content of 17 mg/ml was determined using excitation wavelengths from 235 nm to 500 nm, stepping through at 4.4 nm intervals. Emissions were collected from 275 nm to 760 nm. Data was collected with the Fluorolog®-3 analytical spectrofluorometer. The contour fingerprint spectra are shown in FIGS. 10A-10D for various bacterial loading levels including $10^2$ CFU/mL (FIG. 10A), $10^4$ CFU/mL (FIG. 10B), $10^6$ CFU/mL (FIG. 10C) and the human plasma alone (FIG. 10D).

Figure 11B:
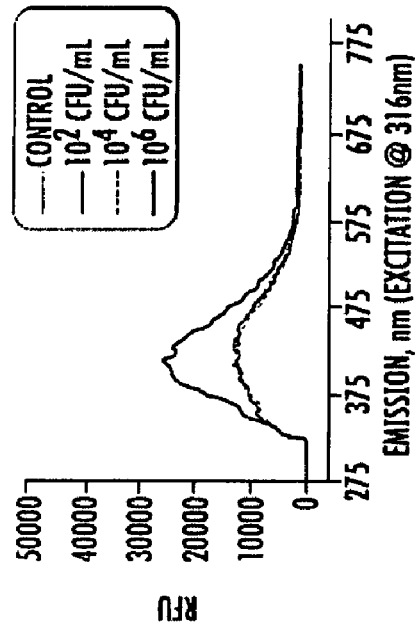
FIG. 11 graphically illustrates the emission spectra of plasma having a protein content of 17 mg/mL (Control), and *S. aureus* in the plasma at $10^2$ CFU/mL, $10^4$ CFU/mL, $10^6$ CFU/mL at various excitation wavelengths including 285 nm (FIG. 11A), 316 nm (FIG. 11B), 348 nm (FIG. 11C), and 410 nm (FIG. 11D)
Figure 11D:
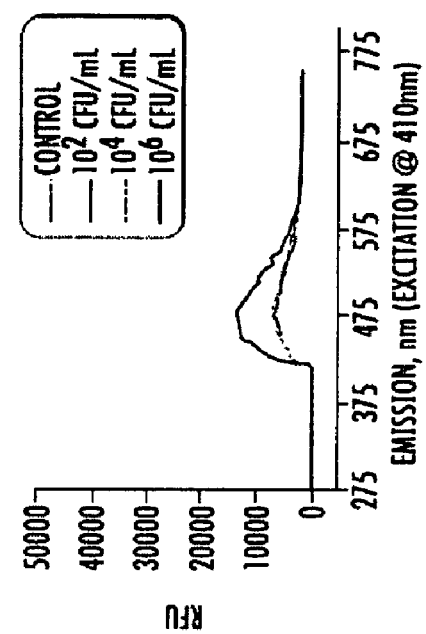
Figure 11A:
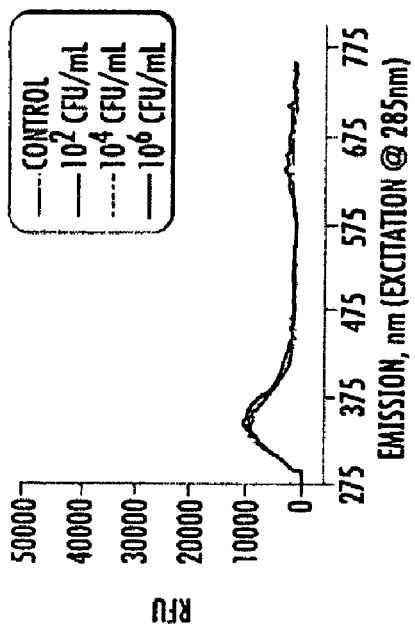
Figure 11C:
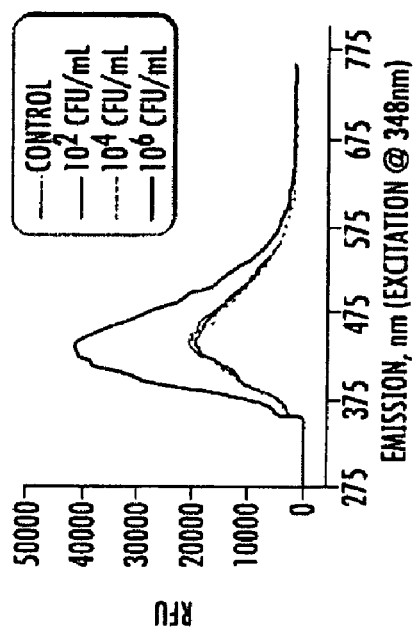

FIG. 11 graphically illustrates the emission spectra for various *S. aureus* bacterial loading levels as compared to the 17 mg/mL protein content plasma for several excitation wavelengths including 285 nm (FIG. 11A), 316 nm (FIG. 11B), 348 nm (FIG. 11C), and 410 nm (FIG. 11D). As may be seen, at *S. aureus* bacterial load of $10^6$ CFU/ml, the presence of the bacteria may be clearly seen.

Example 6

Figure 12:
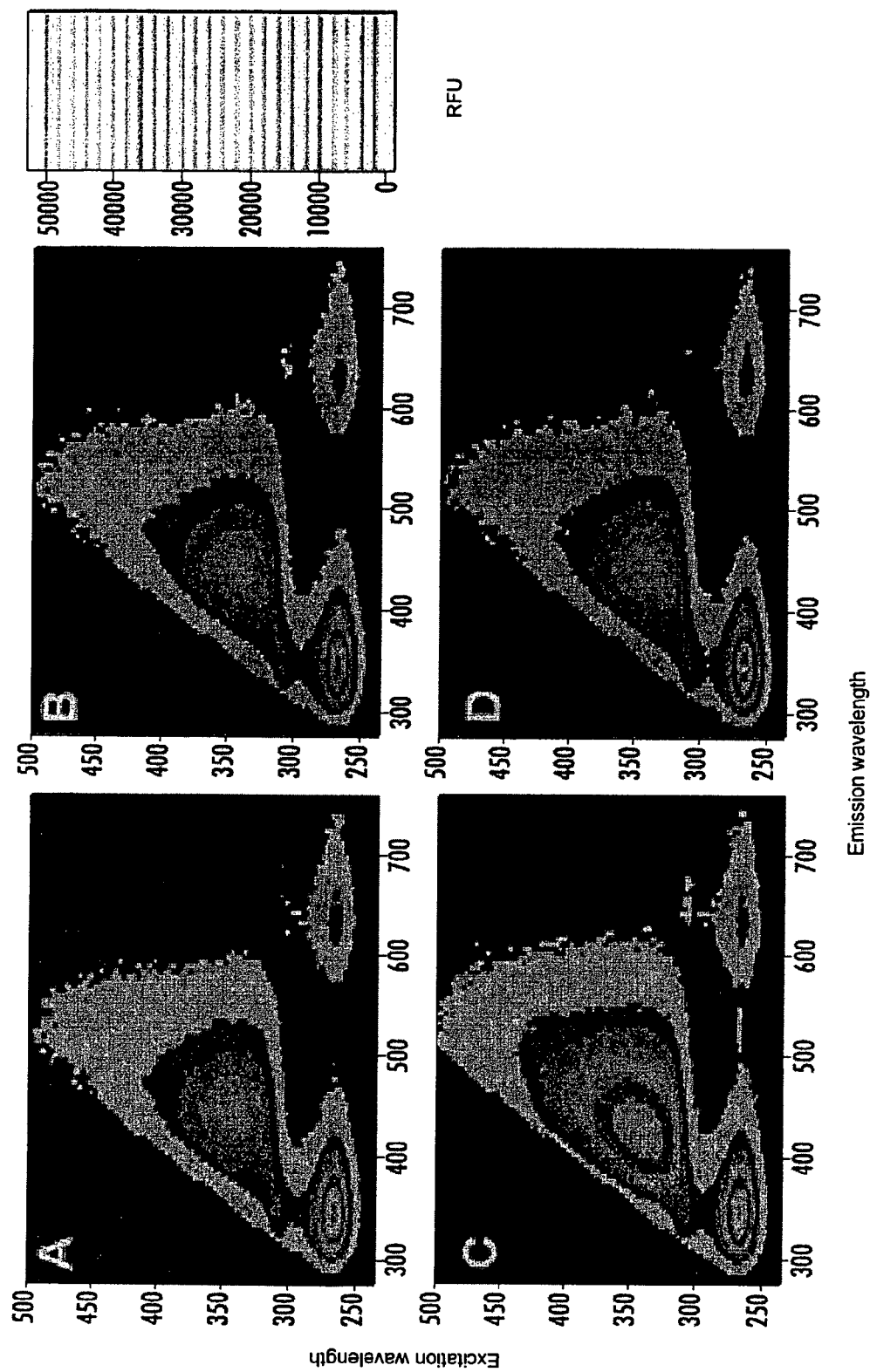
FIG. 12 illustrates contour excitation/emission fingerprint spectra for *P. aeruginosa* in plasma having a protein content of 17 mg/mL at various loading concentrations including $10^2$ CFU/mL (FIG. 12A), $10^4$ CFU/mL (FIG. 12B), $10^6$ CFU/mL (FIG. 12C), and the plasma alone (FIG. 12D)

Example 5 was repeated with *P. aeruginosa* at $10^6$, $10^4$, and $10^2$ CFU/ml in human plasma having a protein content of 17 mg/ml. Data was collected with the Fluorolog®-3 analytical spectrofluorometer. The contour fingerprint spectra are shown in FIGS. 12A-12D for various *P. aeruginosa* bacterial loading levels including $10^2$ CFU/mL (FIG. 12A), $10^4$ CFU/mL (FIG. 12B), $10^6$ CFU/mL (FIG. 12C) and the human plasma alone (FIG. 12D).

Figure 13B:
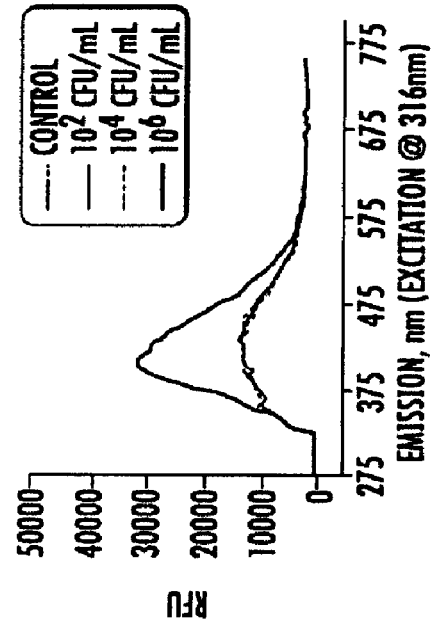
FIG. 13 graphically illustrates the emission spectra of plasma having a protein content of 17 mg/mL (Control), and *P. aeruginosa* in the plasma at $10^2$ CFU/mL, $10^4$ CFU/mL, $10^6$ CFU/mL at various excitation wavelengths including 285 nm (FIG. 13A), 316 nm (FIG. 13B), 348 nm (FIG. 13C), and 410 nm (FIG. 13D)
Figure 13D:
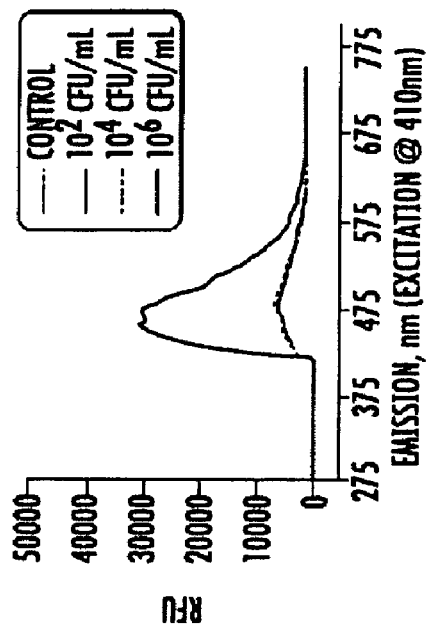
Figure 13A:
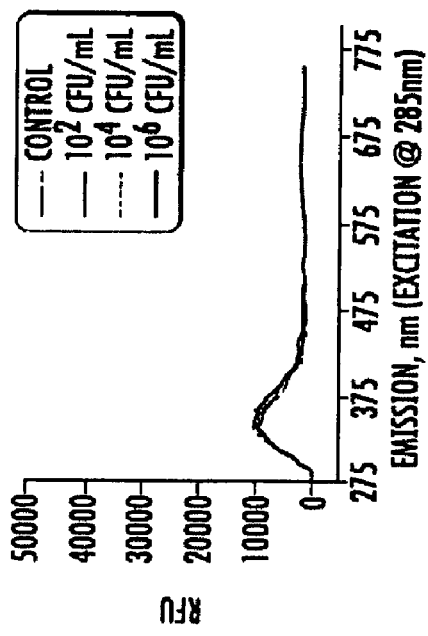
Figure 13C:
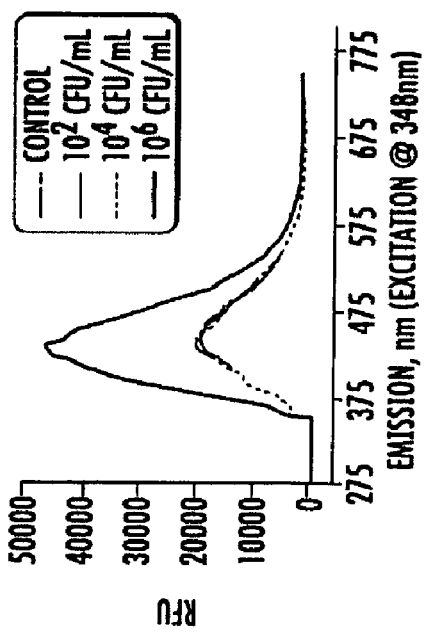

FIG. 13 graphically illustrates the emission spectra for various *P. aeruginosa* bacterial loading levels as compared to the 17 mg/mL protein content plasma for several excitation wavelengths including 285 nm (FIG. 13A), 316 nm (FIG. 13B), 348 nm (FIG. 13C), and 410 nm (FIG. 13D). As may be seen, at bacterial load of $10^6$ CFU/ml, the presence of the *P. aeruginosa* may be clearly seen.

FIGS. 14A-14D compare the results for Examples 5 (*S. aureus*) and 6 (*P. aeruginosa*) across the different bacterial loading concentrations and at various excitation and emission wavelengths including excitation: 285 nm, emission: 345 nm (FIG. 14A), excitation: 316 nm, emission: 405 nm (FIG. 14B), excitation: 348 nm, emission: 435 nm (FIG. 14C), and excitation: 410 nm, emission: 475 nm (FIG. 14D). As may be seen, at bacterial concentrations of $10^6$ CFU/mL, the presence of the bacteria is clearly discernable.

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A method for detecting the presence or amount of a pathogenic bacterium that is a source of a hospital acquired infection comprising:
   locating the end of an optical fiber in a wound or surgical site;
   maintaining the end of the optical fiber in the wound or surgical site throughout a healing process of the wound or surgical site;
   transmitting an excitation signal through a fiber optic cable to the wound or surgical site;
   contacting any bacterial pathogen present with the excitation signal;
   transmitting an autofluorescent emission signal from the bacterial pathogen to a portable detector; and
   determining the presence or amount of the pathogenic bacterium that is a source of a hospital acquired infection in the wound or surgical site based on the autofluorescent emission signal.

2. The method according to claim 1, further comprising transmitting information regarding the presence or amount of the pathogenic bacterium in the wound or surgical site to a receiver.

3. The method according to claim 2, wherein the information is transmitted to the receiver by use of a wireless transmission system.

4. The method according to claim 1, further comprising locating the fiber optic cable in an in vivo environment in conjunction with a medical device.

5. The method according to claim 1, further comprising converting the autofluorescent emission signal to at least one of a visual and an audible signal.

6. The method according to claim 1, wherein the fiber optic cable contains a first optical fiber for transmitting the excitation signal and a second optical fiber for transmitting the autofluorescent emission signal.

7. The method according to claim 1, further comprising determining the presence or concentration of a second bacterium in the environment.

8. The method according to claim 1, wherein a signaling device emits a signal upon determination that the amount of the pathogenic bacterium has exceeded a concentration of about $10^5$ colony forming units per millimeter.

9. A portable device for detecting the amount of a pathogenic bacterium that is a source of a hospital acquired infection comprising:
   a portable enclosure containing a power source, an excitation energy source, an optical detector, a signal processor, and a signaling device for emitting a signal upon detection of the pathogenic bacterium in a wound or surgical site, wherein the signaling device emits a signal upon detection of a bacterial concentration of the pathogenic bacterium greater than about $10^5$ colony forming units per millimeter;
   a connecting device for attaching the enclosure to the clothing or body of a wearer; and
   a fiber optic cable for inserting into the wound or surgical site, the fiber optic cable being in optical communication with the excitation energy source, the fiber optic cable extending for a length exterior to the enclosure, the fiber optic cable including an end configured to be maintained within the wound or surgical site throughout a healing process.

10. The device of claim 9, the enclosure further including a transmitter for transmitting a signal containing information regarding the amount of the bacteria in the wound or surgical site to a receiver.

11. The device of claim 10, wherein the transmitter is a wireless transmitter.

12. The device of claim 9, wherein the fiber optic cable contains only a single optical fiber.

13. The device of claim 9, wherein the fiber optic cable contains a plurality of optical fibers.

14. The device of claim 13, the fiber optic cable comprising a first optical fiber in optical communication with the excitation energy source, and a second optical fiber in optical communication with the optical detector.

15. The device of claim 9, the device further comprising a second fiber optic cable in optical communication with the optical detector.

16. The device of claim 9, wherein the excitation source delivers a single excitation wavelength to the fiber optic cable.

17. The device of claim 9, wherein the excitation source delivers multiple excitation wavelengths to the fiber optic cable.

18. The device of claim 9, wherein the signaling device emits a plurality of signals upon detection of the pathogenic bacterium in an environment.

19. The device of claim 9, wherein the connecting device is for connecting the enclosure to a piece of clothing.

20. The device of claim 9, wherein the connecting device comprises an adhesive.

21. The device of claim 20, wherein the connecting device is for connecting the enclosure to a wearer's skin.

22. The device of claim 13, the device further comprising a plurality of notch filters.

* * * * *